United States Patent [19]

Fischer

[11] Patent Number: Plant 6,640

[45] Date of Patent: Feb. 28, 1989

[54] AFRICAN VIOLET PLANT NAMED BLUE WATERS

[76] Inventor: Arnold Fischer, Kahlendamm 22, 3000 Hanover 51, Fed. Rep. of Germany

[21] Appl. No.: 85,121

[22] Filed: Aug. 13, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of African violet named Blue Waters, characterized by its large, single dark violet blue flowers, dark green foliage, compact growth habit, and its floriferousness.

1 Drawing Sheet

1

The present invention comprises a new and distinct cultivar of African violet plant, botanically known as *Saintpaulia ionantha,* named Blue Waters.

The new cultivar is a product of a planned breeding program carried out by applicant in Hannover, Federal Republic of Germany. The basic objective of the breeding program was to create a new African violet cultivar having large, single dark violet-blue flowers, compact plant habit, light green foliage and a highly floriferous habit.

The new cultivar was originated from a cross made by applicant in the controlled breeding program. Both the female (or seed) and the male (or pollen) parents were unnamed seedlings not specifically identifiable.

Blue Waters was discovered and selected by applicant as a flowering plant within the progeny of the stated cross in a controlled environment in Hannover, Federal Republic of Germany. Asexual reproduction of the new cultivar of leaf cuttings, as performed by me at Hannover, Federal Republic of Germany, has demonstrated that the combination of characteristics as herein disclosed for the new cultivar are firmly fixed and retained through successive generations of asexual reproduction.

Blue Waters has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Blue Waters which in combination distinguish this African violet as a new and distinct cultivar:

(1) Large dark blue single zygomorphic rotate flowers up to 38 mm in diameter.

(2) Compact rosette habit with flowers held erect on strong upright peduncles.

(3) Very floriferous, with flowers continuing to open for many weeks after the onset of flowering.

(4) Dark green, pubescent foliage which is cordate with crenate margins.

(5) Suitable for production in 10 cm pots, finishing in 9–13 weeks when started from a 2¼" plantlet.

The new cultivar is most similar to the cultivar Big Star, disclosed in U.S. Plant Pat. No. 5,066. Blue Waters is principally distinguished from Big Star by its higher

2 degree of floriferousness, and its smaller and darker colored flowers.

The accompanying photographic drawing shows a typical specimen plant of the new cultivar. The photograph is in black and white, with a single flower being colored to accurately depict true flower color as depicted below.

In the following description, color references are made to The Royal Horticultural Society Colour Chart (R.H.S.), except where general colors of ordinary significance are referred to. Color values were taken under fluorescent light conditions at approximately 12:50 p.m. in Parrish, Fla.

Botanical classification: *Saintpaulia ionantha,* Ramat., cv. Blue Waters.

Parentage: Unknown.

Propagation: The new cultivar holds its distinguishing characteristics through successive propagations by leaf cuttings.

Plant: From 6 cm to 10 cm tall when grown in pots, and approximately 20 cm in diameter when fully grown. The growth rate is vigorous, and the general shape of the fully growth plant is round.

*Leaves.*—Quantity: Abundant. Shape: Cordate with crenate margin. Diameter: Up to 6 cm. Texture: Pubescent, glossy. Ribs and Veins: Pinnate. Color (upper side): 147 A. Color (under side): 48 D, with some veins having a purplish cast. Petioles: Light green-purple.

*Flowers.*—Buds: Size: Up to 7 mm×7 mm. Shape: Round. Rate of opening: Normal. Sepals: Shape: Lanceolate. Color: Green-purple. Phyllaries: 2, lanceolate. Color: 147 A (upperside); underside purple-green. Calyx: Shape: Funnel. Size: About 11 mm in diameter. Aspect: Hairy. Peduncle: Length: Up to 8 cm. Character: Erect and rigid. Color: Purple-green.

*Individual flowers.*—Number of petals: 5. Size: Up to 38 mm across and 10 mm deep. Shape: Cup shaped when bloom first opens, becoming flat as bloom matures. Color (upper side): 89 B. Color (under side): 89 B. Flowers fade slightly as they age. The flower color may vary somewhat depending upon the amount of light, fertilizer, temperature and other growing conditions. Borne: In a cyme on 60–80 mm peduncles. Flowering habit: Flowers profusely and intermittently year round, with blooms lasting 2–3 weeks after which petals dry up but do not drop. Finishes in 19–12 weeks when a $2\frac{1}{4}''$ plantlet is placed in a 10 cm pot.

*Reproductive organs.*—Stamens: Stamens borne singly on one side of ovary. 2 anthers basifixed. Anthers: 2 mm × 2 mm, yellow. Filaments: 2 mm, purple and green. Pollen Color: Yellow. Pistels: Number: 1. Styles: 5–7, 7 mm long. Stigma: Sticky, white. Ovaries: Superior.

Disease resistance: No African violet diseases observed to date.

I claim:

1. A new and distinct cultivar of African violet named Blue Waters, as illustrated and described, and particularly characterized by its large, single dark violet blue flowers, dark green foliage, compact growth habit, and its floriferousness.

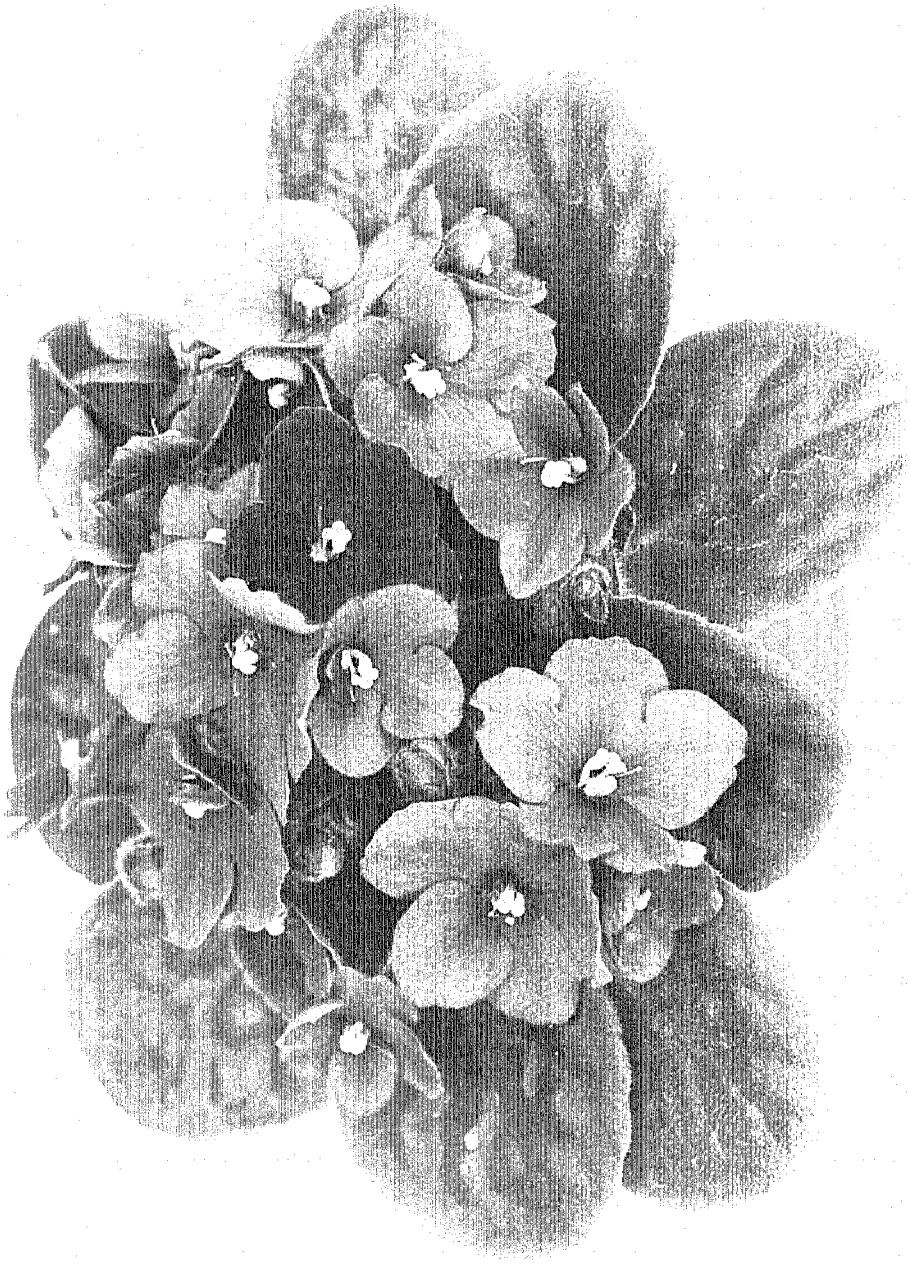

* * * * *